United States Patent
Wang et al.

(10) Patent No.: US 9,632,034 B2
(45) Date of Patent: Apr. 25, 2017

(54) FLUOROGENIC AND CHROMOGENIC SUBSTRATE

(71) Applicant: LI-COR, Inc., Lincoln, NE (US)

(72) Inventors: Ying Wang, Lincoln, NE (US); Xinshe Xu, Lincoln, NE (US); Nisha Padhye, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 0 days.

(21) Appl. No.: 15/068,373

(22) Filed: Mar. 11, 2016

(65) Prior Publication Data

US 2016/0266045 A1 Sep. 15, 2016

Related U.S. Application Data

(60) Provisional application No. 62/133,006, filed on Mar. 13, 2015.

(51) Int. Cl.
| | |
|---|---|
| G01N 21/78 | (2006.01) |
| C12Q 1/28 | (2006.01) |
| G01N 33/58 | (2006.01) |
| G01N 21/76 | (2006.01) |

(52) U.S. Cl.
CPC ............... *G01N 21/78* (2013.01); *C12Q 1/28* (2013.01); *G01N 21/76* (2013.01); *G01N 33/582* (2013.01)

(58) Field of Classification Search
CPC ..................................................... G01N 21/78
USPC ..................................................... 514/224.8
See application file for complete search history.

(56) References Cited

U.S. PATENT DOCUMENTS

| | | | |
|---|---|---|---|
| 5,171,668 A | 12/1992 | Sugiyama | |
| 5,445,755 A | 8/1995 | Convents et al. | |
| 6,432,662 B1 | 8/2002 | Davis et al. | |
| 6,897,036 B2 | 5/2005 | Akhavan-Tafti et al. | |
| 7,855,287 B2 * | 12/2010 | Della Ciana ......... | C07D 279/22 544/35 |
| 8,192,948 B1 | 6/2012 | Feather-Henigan et al. | |

FOREIGN PATENT DOCUMENTS

| | | |
|---|---|---|
| JP | 08038196 | 2/1996 |
| WO | 0155446 | 8/2001 |
| WO | 2015183931 | 12/2015 |

OTHER PUBLICATIONS

International Search Report and Written Opinion for PCT/US2016/022133 filed Mar. 11, 2016, mailed May 20, 2016, 11 pages.

\* cited by examiner

*Primary Examiner* — Taofiq A Solola
(74) *Attorney, Agent, or Firm* — Kilpatrick Townsend and Stockton LLP

(57) ABSTRACT

The present invention provides near-infrared fluorogenic and/or chromogenic formulations, methods, systems and kits. Upon contacting an azine with an oxidant and a peroxidase, the azine is converted to an azine derivative which is both visibly colored and fluorescent. This invention also provides high sensitive methods to detect biological molecules, showing better sensitivity than chemiluminescence methods. Advantageously, the formulation and reaction is free of luminol or luminol derivatives.

20 Claims, 14 Drawing Sheets

Scheme 1

Scheme 1

Scheme 2

Scheme 3

Scheme 4

*Digital imager Fc, chemi channel*

*Digital imager CLX, 700 channel*

Digital imager CLX, 700 channel

Digital imager Fc, chemi channel

Film

PTA

Digital imager CLX, 700 channel

SuperSignal Femto

Digital imager Fc, chemi channel

SuperSignal Femto

Gray film, FLASH

SuperSignal Femto

Gray film, 1 minute

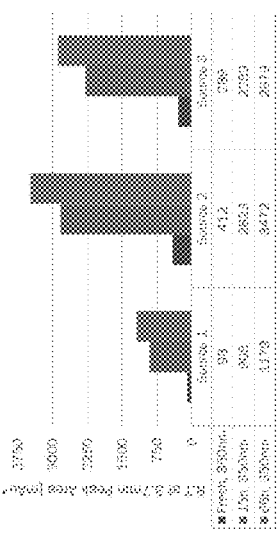
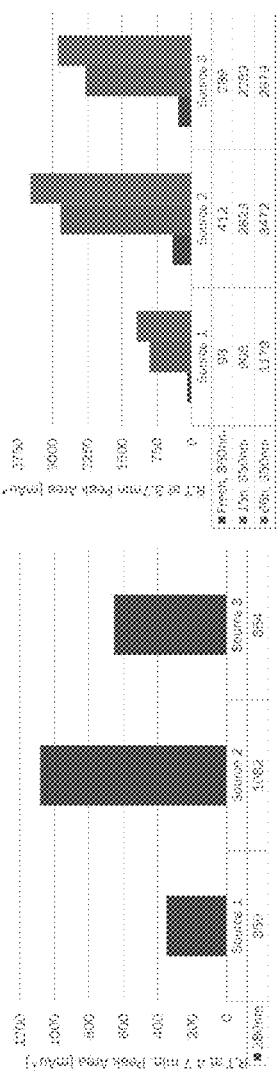
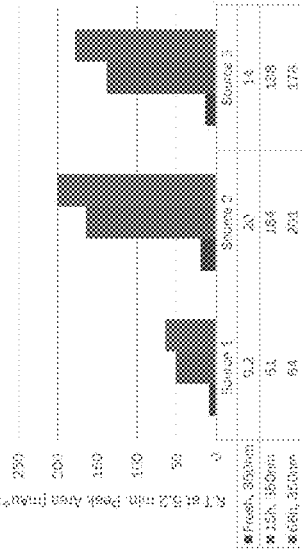

FLUOROGENIC AND CHROMOGENIC SUBSTRATE

CROSS-REFERENCE TO RELATED APPLICATIONS

This application claims priority to U.S. Provisional Patent Application No. 62/133,006, filed Mar. 13, 2015, the teachings of which are incorporated herein by reference in their entirety for all purposes.

BACKGROUND OF THE INVENTION

Detection and quantitation of analytes in assays is important in immunology, microbiology, diagnostics and medicine. Some methods for detecting analytes rely on intrinsic properties of the molecule to be detected. For example, methods for detecting analytes in samples such as chemical analysis, include NMR, high pressure liquid chromatography, gas chromatography, absorbance, fluorescence, chemiluminescence and mass spectrometry. These techniques rely on chemical or physical properties of the molecules being detected (for example optical properties, reactive groups, charge, size, and hydrophobicity).

Other methods for detecting analytes rely on some part of the analyte being recognized by another molecule. For example, methods for detecting nucleic acids often utilize hybridization and complementary base pairing. Other methods rely on the conformation of part of the analyte being recognized by another molecule. Examples of such methods of detection include an antibody binding to an antigen and an aptamer binding to a target epitope region.

Examples of biological assays where these detection methods are utilized are innumerable, and include DNA sequencing, restriction fragment length polymorphism determination, Southern blotting and other forms of DNA hybridization analysis, determination of single-strand conformational polymorphisms, comparative genomic hybridization, mobility-shift DNA binding assays, protein gel electrophoresis, Northern blotting and other forms of RNA hybridization analysis, protein purification, chromatography, immunoprecipitation, protein sequence determination, Western blotting (protein immunoblotting), ELISA and other forms of antibody-based protein detection, isolation of biomolecules for use as antigens to produce antibodies, PCR, RT PCR, differential display of mRNA by PCR, and the like. Protocols for carrying out these and other forms of assays are readily available to those of skill in the art.

Methods that utilize recognition of an analyte by another molecule for detection are important, particularly in biology. One area where there is lack of available systems and useful reagents is in the area of near-infrared chemifluorescent systems. Chemifluorescent reactions occur very fast. However, it would be advantageous to be able to visualize a chemifluorescent reaction with the naked eye through a simultaneous chromogenic reaction. There is a need in the art for new chemifluorescent reagents that also have a chromogenic reaction associated with them. The present invention satisfies these and other needs.

BRIEF SUMMARY OF THE INVENTION

The present invention relates to chemifluorescent reagents that also have a chromogenic functionality (e.g., visible to the naked eye or visibly colored) associated with them, these reagents being useful in assays of peroxidase activity. As such, in one embodiment, the present invention provides a formulation comprising, consisting essentially of, or consisting of, a) a first part and b) a second part:

a) the first part comprising one or more azines; and
b) the second part comprising an oxidant.

In another embodiment, the present invention provides a method for producing a fluorogenic and/or chromogenic reaction, the method comprising, consisting essentially of, or consisting of admixing:

a) a first part of a formulation comprising one or more azines; and
b) a second part comprising an oxidant.

In still yet another embodiment, the present invention provides a kit for preparing a fluorogenic and/or chromogenic reaction, the kit comprising, consisting essentially of, or consisting of:

a) a first part comprising one or more azines;
b) the second part comprising an oxidant; and instructions for use.

These and other embodiments, objects and advantages will become more apparent with the detailed description and drawings which follow.

BRIEF DESCRIPTION OF THE DRAWINGS

FIG. 5A shows the chemiluminescent signal from SuperSignal™ West Femto Substrate (Thermo Fisher). FIG. 5B shows the blot treated with formulation consisting of 0.65 mM PTA. FIG. 5C shows the blot treated with formulation consisting of 0.35 mM PTA. FIG. 5D shows the blot treated with formulation consisting of 0.15 mM PTA.

FIG. 6A shows 7 protein bands on the membrane treated with SuperSignal™ West Femto Substrate. FIG. 6B shows 9 protein bands on an identical membrane treated with PTA substrate.

FIG. 7A shows a digital image of the TMB substrate blot and FIG. 7B shows a digital image of the chromogenic PTA substrate blot. FIG. 7C shows a digital scanner image of the TMB substrate blot and FIG. 7D shows a digital scanner image of the chromogenic PTA substrate blot. FIG. 7E shows an inverted image of the TMB substrate blot generated by Image Studio software and FIG. 7F shows an inverted image of the chromogenic PTA substrate blot. FIG. 7G represents a plot of the intensity of chromogenic TMB substrate versus chromogenic PTA substrate. The data shows that the chromogenic PTA substrate is 2-fold more sensitive compared to the TMB substrate.

FIGS. 12A-C show HPLC detection of oxidation impurities in the solubilizers (A); time and impurity correlation on the progress of oxidation of PTAS (B) and PTA (C).

DETAILED DESCRIPTION OF THE INVENTION

I. Definitions

Figure 1:
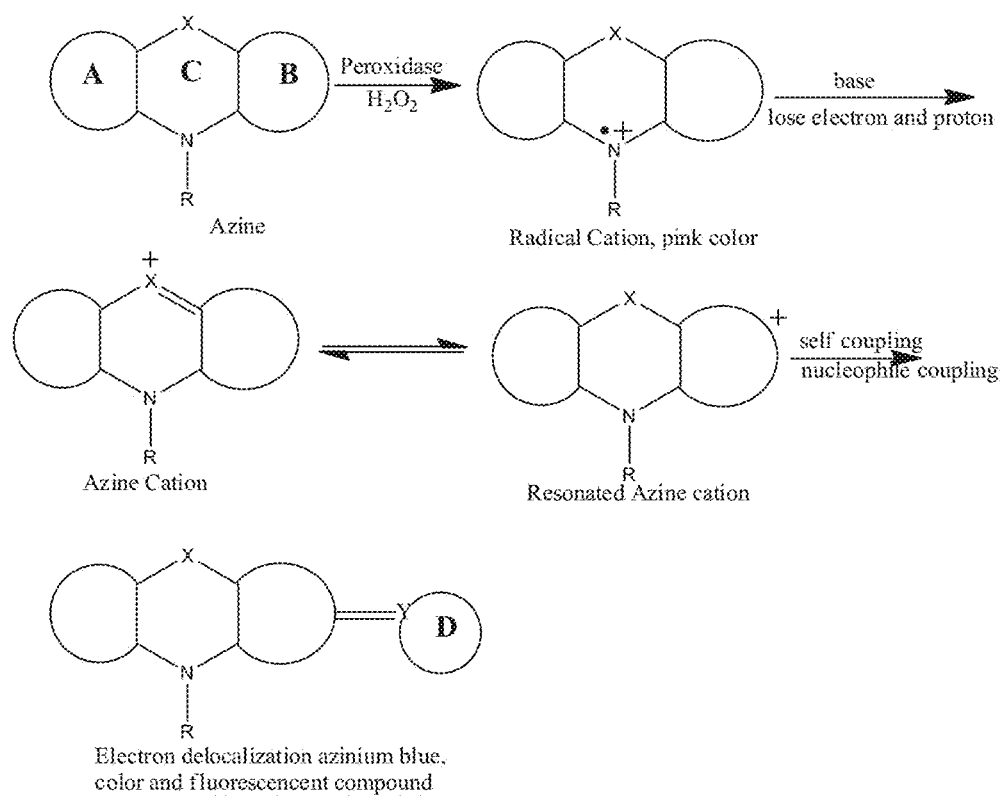
FIG. 1 illustrates Scheme 1, which shows one embodiment of the present invention.
Figure 2:
FIG. 2 illustrates Scheme 2, which shows one embodiment of the present invention.
Figure 2:
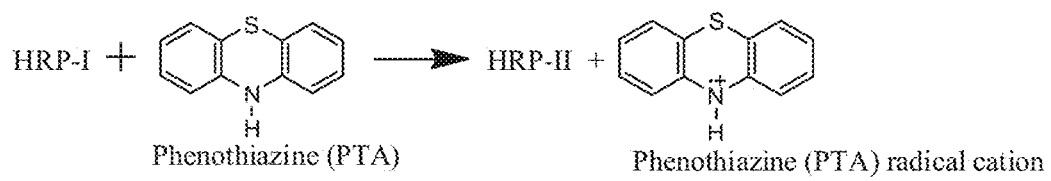
Figure 2:
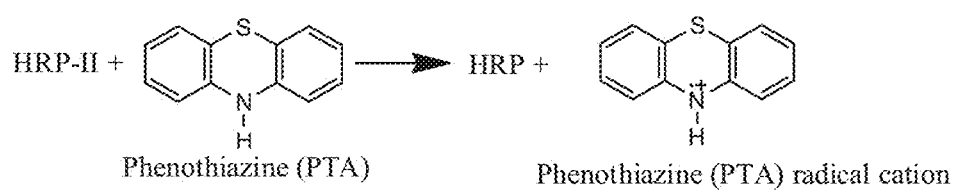
Figure 2:
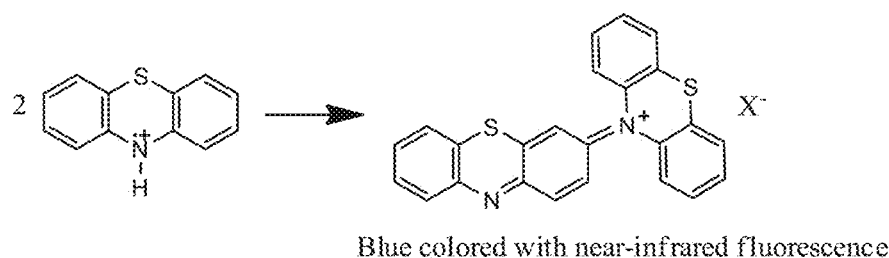

The terms "a," "an," or "the" as used herein not only include aspects with one member, but also include aspects with more than one member.

The term "about" as used herein to modify a numerical value indicates a defined range around that value. If "X" were the value, "about X" would indicate a value from 0.9X to 1.1X, and more preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g, "0.98X."

The term "biological assay" is a method of biological analysis, in which a biological substrate of interest is reacted with chemicals or biochemicals, where the reaction can be used to characterize the substrate (e.g, by function, presence or absence, etc.).

The term "oxidant" includes substances which are oxidizing agents or a substance which accepts an electron from another species. An oxidant gains electrons during a reaction and is reduced.

II. Embodiments

The present invention provides near-infrared fluorogenic and/or chromogenic formulations, methods, systems and kits that utilize an oxidation reaction of an azine derivative to effectuate detection. The oxidation reaction can be an enzyme-catalyzed deposition of the azine. In certain aspects, upon contacting the azine with an oxidant and a peroxidase, the azine is converted to an azine derivative, which is both visibly colored and fluorescently detectable. Advantageously, the formulation and reaction are free of luminol or a luminol derivative i.e., there is no luminol present in the reaction mixture. The oxidation of the azine is preferably performed in the presence of an oxidation catalyst such as a peroxidase.

In one embodiment, the present invention provides a formulation, the formulation comprising a) a first part and b) a second part:

a) the first part comprising one or more azines; and b) the second part comprising an oxidant.

In one aspect, the one or more azines is 10H-phenothiazine (PTA). In another aspect, the one or more azines is a mixture of PTA and sodium 3-(phenothiazine-10-yl)propane-1-sulfonate (PTAS). In certain aspects, the one or more azine(s) is a fluorogenic and chromogenic substrate.

In certain aspects, the one or more azines which are suitable for the present invention are compounds of formula (Ia-Id):

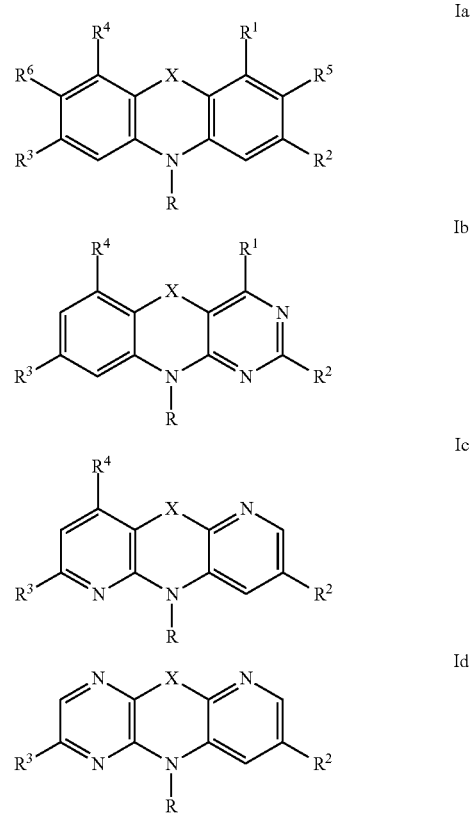

wherein R, $R^1$, $R^2$, $R^3$, $R^4$, $R^5$, $R^6$ and X are defined as follows: R is hydrogen, an amido, an amido wherein the N can bear a water soluble group such as PEG (ethylene oxide), hydroxyl, sulfonato, amino, carboxyl, an alkyl group having 1 to 12 carbons, preferably 1 to 6 carbon atoms or alkanoyl group having 1 to 12 carbons, preferably 1-6 carbon atoms, wherein each may have a substituent, or an alkene group having 2 to 12 carbons, preferably 2-6 carbon atoms, which may have a substituent, $R^1$ to $R^6$, which substituent may be the same or different and each represents hydrogen, an alkyl group having 1 to 12 carbons, preferably 1-6 carbon atoms, which may have a substituent, amino, or a halogen, and X represents oxygen or sulfur or nitrogen. X can also be C=O, or $CR^1R^2$, or $NR^1$.

In certain aspects, R can include water insoluble groups, wherein each may have alkyl groups with tertiary amine substitutions as for example: 3-(2-chloro-10H-phenothiazin-10-yl)-N,N-dimethyl-propan-1-amine:

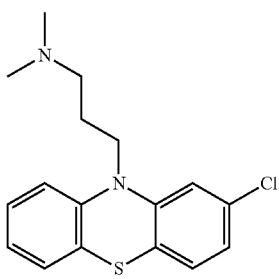 [SMILES: CN(C)CCCN1c2ccccc2Sc2ccc(Cl)cc21]

Water insoluble phenothiazine derivatives (as above) can be oxidized, and thereafter advantageously precipitate on protein bands for fluorescence detection. Depending on the degree of oxidization, the fluorescence can be detected from visible to near-infrared.

Specific examples of the compounds represented by formula (I-a) include the following:

| | |
|---|---|
| 10H-phenothiazine (PTA) | sodium 3-(phenothiazine-10-yl)propane-1-sulfonate (PTAS) |
| N-methylphenoxazine, | 6-propylphenoxazine-10-yl-propylsulfonate, |
| N-ethylphenoxazine, | 8-propylphenoxazine-10-yl-propylsulfonate, |
| N-propylphenoxazine, | 1,3-dipropylphenoxazine-10-yl-propylsulfonate, |
| sodium phenoxazine-10-yl-propanesulfonate, | 1,6-dipropylphenoxazine-10-yl-propylsulfonate, |
| sodium phenoxazine-10-yl-2,4-dimethyl-1,3-butadienesulfonate, | 1,8-dipropylphenoxazine-10-yl-propylsulfonate, |
| 1-methylphenoxazine-10-yl-propylsulfonate, | 3,6-dipropylphenoxazine-10-yl-propylsulfonate, |
| 3-methylphenoxazine-10-yl-propylsulfonate, | 3,8-dipropylphenoxazine-10-yl-propylsulfonate, |
| 6-methylphenoxazine-10-yl-propylsulfonate, | 6,8-dipropylphenoxazine-10-yl-propylsulfonate, |
| 8-methylphenoxazine-10-yl-propylsulfonate, | 1,3,6-tripropylphenoxazine-10-yl-propylsulfonate, |
| 1,3-dimethylphenoxazine-10-yl-propylsulfonate, | 1,3,8-tripropylphenoxazine-10-yl-propylsulfonate, |
| 1,6-dimethylphenoxazine-10-yl-propylsulfonate, | 1,6,8-tripropylphenoxazine-10-yl-propylsulfonate, |
| 1,8-dimethylphenoxazine-10-yl-propylsulfonate, | 1-butylphenoxazine-10-yl-propylsulfonate, |
| 3,6-dimethylphenoxazine-10-yl-propylsulfonate, | 3-butylphenoxazine-10-yl-propylsulfonate, |
| 3,8-dimethylphenoxazine-10-yl-propylsulfonate, | 6-butylphenoxazine-10-yl-propylsulfonate, |
| 6,8-dimethylphenoxazine-10-yl-propylsulfonate, | 8-butylphenoxazine-10-yl-propylsulfonate, |
| 1,3,6-trimethylphenoxazine-10-yl-propylsulfonate, | 1,3-dibutylphenoxazine-10-yl-propylsulfonate, |
| 1,3,8-trimethylphenoxazine-10-yl-propylsulfonate, | 1,6-dibutylphenoxazine-10-yl-propylsulfonate, |
| 1,6,8-trimethylphenoxazine-10-yl-propylsulfonate, | 1,8-dibutylphenoxazine-10-yl-propylsulfonate, |
| 1-ethylphenoxazine-10-yl-propylsulfonate, | 3,6-dibutylphenoxazine-10-yl-propylsulfonate, |
| 3-ethylphenoxazine-10-yl-propylsulfonate, | 3,8-dibutylphenoxazine-10-yl-propylsulfonate, |
| 6-ethylphenoxazine-10-yl-propylsulfonate, | 6,8-dibutylphenoxazine-10-yl-propylsulfonate, |
| 8-ethylphenoxazine-10-yl-propylsulfonate, | 1,3,6-tributylphenoxazine-10-yl-propylsulfonate, |
| 1,3-diethylphenoxazine-10-yl-propylsulfonate, | 1,3,8-tributylphenoxazine-10-yl-propylsulfonate, |
| 1,6-diethylphenoxazine-10-yl-propylsulfonate, | 1,6,8-tributylphenoxazine-10-yl-propylsulfonate, |
| 1,8-diethylphenoxazine-10-yl-propylsulfonate, | 1-chlorophenoxazine-10-yl-propylsulfonate, |
| 3,6-diethylphenoxazine-10-yl-propylsulfonate, | 3-chlorophenoxazine-10-yl-propylsulfonate, |
| 3,8-diethylphenoxazine-10-yl-propylsulfonate, | 6-chlorophenoxazine-10-yl-propylsulfonate, |
| 6,8-diethylphenoxazine-10-yl-propylsulfonate, | 8-chlorophenoxazine-10-yl-propylsulfonate, |
| 1,3,6-triethylphenoxazine-10-yl-propylsulfonate, | 1-bromophenoxazine-10-yl-propylsulfonate, |
| 1,3,8-triethylphenoxazine-10-yl-propylsulfonate, | 3-bromophenoxazine-10-yl-propylsulfonate, |
| 1,6,8-triethylphenoxazine-10-yl-propylsulfonate, | 6-bromophenoxazine-10-yl-propylsulfonate, |

| | |
|---|---|
| 1-propylphenoxazine-10-yl-propylsulfonate, | 8-bromophenoxazine-10-yl-propylsulfonate. |
| 3-propylphenoxazine-10-yl-propylsulfonate, | Sodium 3-(phenothiazine-10-yl)propionate |
| 2-[4-[3-(2-chlor-10H-phenothiazin-10-yl)propyl]piperazie-1-yl]ethanol | 2-chloro-10-(3-diethylaminopropionyl)-phenothiazine |
| 3,7-bis(dimethylamino)-10H-phenothiazin-10-yl((phenyl)methanone (BLMB) | 3-(2-chloro-10H-phenothiazin-10-yl)-N,N-dimethyl-propan-1-amine, |
| 2-[4-[3-(2-chlor-10H-phenothiazin-10-yl)propyl]piperazie-1-yl]ethanol, | 2-chloro-10-[3-(4-methyl-1-piperazinyl)propyl]-10H-phenothiazine, |
| 2-chloro-10-(3-diethylaminopropionyl)-phenothiazine, | N,N-dimethyl-3-(10H-phenothiazin-10-yl)-propan-1-amine, |
| 1-{10-[3-(Dimethylamino)propyl]-10H-phenothiazin-2-yl}ethanone, | 10-{2-[(RS)-1-Methylpiperidin-2-yl]ethyl}-2-methylsulfanylphenothiazine, |
| N,N,2-trimethyl-3-phenothiazin-10-yl-propan-1-amine, | 10-[3-(4-methylpiperazin-1-yl)propyl]-2-(trifluoromethyl)-10H-phenothiazine |

Each of the above compounds can be a phenothiazine instead of a phenoxazine such as 1-propylphenthiazine-10-yl-propylsulfonate in lieu of 1-propylphenoxazine-10-yl-propylsulfonate. Likewise, a phenothiazine above can be a phenoxazine.

Specific examples of the compounds represented by formula (I-b) are as follows:

| | |
|---|---|
| N-methylpyrimidylphenoxazine, | 8-propylpyrimidylphenoxazine-10-yl-propylsulfonate, |
| N-ethylpyrimidylphenoxazine, | 1,3-dipropylpyrimidylphenoxazine-10-yl-propylsulfonate, |
| N-propylpyrimidylphenoxazine, | 1,6-dipropylpyrimidylphenoxazine-10-yl-propylsulfonate, |
| sodium pyrimidylphenoxazine-10-yl-propanesulfonate, | 1,8-dipropylpyrimidylphenoxazine-10-yl-propylsulfonate, |
| sodium pyrimidylphenoxazine-10-yl-2,4-dimethyl-1,3-butadienesulfonate, | 3,6-dipropylpyrimidylphenoxazine-10-yl-propylsulfonate, |
| 1-methylpyrimidylphenoxazine-10-yl-propylsulfonate, | 3,8-dipropylpyrimidylphenoxazine-10-yl-propylsulfonate, |
| 3-methylpyrimidylphenoxazine-10-yl-propylsulfonate, | 6,8-dipropylpyrimidylphenoxazine-10-yl-propylsulfonate, |
| 6-methylpyrimidylphenoxazine-10-yl-propylsulfonate, | 1,3,6-tripropylpyrimidylphenoxazine-10-yl-propylsulfonate, |
| 8-methylpyrimidylphenoxazine-10-yl-propylsulfonate, | 1,3,8-tripropylpyrimidylphenoxazine-10-yl-propylsulfonate, |
| 1,3-dimethylpyrimidylphenoxazine-10-yl-propylsulfonate, | 1,6,8-tripropylpyrimidylphenoxazine-10-yl-propylsulfonate, |
| 1,6-dimethylpyrimidylphenoxazine-10-yl-propylsulfonate, | 1-butylpyrimidylphenoxazine-10-yl-propylsulfonate, |
| 1,8-dimethylpyrimidylphenoxazine-10-yl-propylsulfonate, | 3-butylpyrimidylphenoxazine-10-yl-propylsulfonate, |
| 3,6-dimethylpyrimidylphenoxazine-10-yl-propylsulfonate, | 6-butylpyrimidylphenoxazine-10-yl-propylsulfonate, |
| 3,8-dimethylpyrimidylphenoxazine-10-yl-propylsulfonate, | 8-butylpyrimidylphenoxazine-10-yl-propylsulfonate, |
| 6,8-dimethylpyrimidylphenoxazine-10-yl-propylsulfonate, | 1,3-dibutylpyrimidylphenoxazine-10-yl-propylsulfonate, |
| 1,3,6-trimethylpyrimidylphenoxazine-10-yl-propylsulfonate, | 1,6-dibutylpyrimidylphenoxazine-10-yl-propylsulfonate, |
| 1,3,8-trimethylpyrimidylphenoxazine-10-yl-propylsulfonate, | 1,8-dibutylpyrimidylphenoxazine-10-yl-propylsulfonate, |
| 1,6,8-trimethylpyrimidylphenoxazine-10-yl-propylsulfonate, | 3,6-dibutylpyrimidylphenoxazine-10-yl-propylsulfonate, |
| 1-ethylpyrimidylphenoxazine-10-yl-propylsulfonate, | 3,8-dibutylpyrimidylphenoxazine-10-yl-propylsulfonate, |
| 3-ethylpyrimidylphenoxazine-10-yl-propylsulfonate, | 6,8-dibutylpyrimidylphenoxazine-10-yl-propylsulfonate, |
| 6-ethylpyrimidylphenoxazine-10-yl-propylsulfonate, | 1,3,6-tributylpyrimidylphenoxazine-10-yl-propylsulfonate, |
| 8-ethylpyrimidylphenoxazine-10-yl-propylsulfonate, | 1,3,8-tributylpyrimidylphenoxazine-10-yl-propylsulfonate, |
| 1,3-diethylpyrimidylphenoxazine-10-yl-propylsulfonate, | 1,6,8-tributylpyrimidylphenoxazine-10-yl-propylsulfonate, |
| 1,6-diethylpyrimidylphenoxazine-10-yl- | 1-chloropyrimidylphenoxazine-10-yl- |

-continued

| | |
|---|---|
| propylsulfonate, | propylsulfonate, |
| 1,8-diethylpyrimidylphenoxazine-10-yl-propylsulfonate, | 3-chloropyrimidylphenoxazine-10-yl-propylsulfonate, |
| 3,6-diethylpyrimidylphenoxazine-10-yl-propylsulfonate, | 6-chloropyrimidylphenoxazine-10-yl-propylsulfonate, |
| 3,8-diethylpyrimidylphenoxazine-10-yl-propylsulfonate, | 8-chloropyrimidylphenoxazine-10-yl-propylsulfonate, |
| 6,8-diethylpyrimidylphenoxazine-10-yl-propylsulfonate, | 1-bromopyrimidylphenoxazine-10-yl-propylsulfonate, |
| 1,3,6-triethylpyrimidylphenoxazine-10-yl-propylsulfonate, | 3-bromopyrimidylphenoxazine-10-yl-propylsulfonate, |
| 1,3,8-triethylpyrimidylphenoxazine-10-yl-propylsulfonate, | 6-bromopyrimidylphenoxazine-10-yl-propylsulfonate, |
| 1,6,8-triethylpyrimidylphenoxazine-10-yl-propylsulfonate, | 8-bromopyrimidylphenoxazine-10-yl-propylsulfonate. |
| 1-propylpyrimidylphenoxazine-10-yl-propylsulfonate, | 2-(10H-phenoxazine-10-yl)ethanol |
| 3-propylpyrimidylphenoxazine-10-yl-propylsulfonate, | 3-(10H-phenoxazine-10-yl)propanoic acid |
| 6-propylpyrimidylphenoxazine-10-yl-propylsulfonate, | 3-(10H-phenoxazine-10-yl)propylamine |

Each of the above compounds can be a pyrimidylphenothiazine instead of a pyrimidylphenoxazine such as 6-propylpyrimidylphenothiazine-10-yl-propylsulfonate in lieu of 6-propylpyrimidylphenoxazine-10-yl-propyl sulfonate.

Specific examples of the compounds represented by formula (I-c) are as follows:

| | |
|---|---|
| N-methylpyridylphenoxazine, | 6-propylpyridylphenoxazine-10-yl-propylsulfonate, |
| N-ethylpyridylphenoxazine, | 8-propylpyridylphenoxazine-10-yl-propylsulfonate, |
| N-propylpyridylphenoxazine, | 3,6-dipropylpyridylphenoxazine-10-yl-propylsulfonate, |
| sodium pyridylphenoxazine-10-yl-propanesulfonate, | 3,8-dipropylpyridylphenoxazine-10-yl-propylsulfonate, |
| sodium pyridylphenoxazine-10-yl-2,4-dimethyl-1,3-butadienesulfonate, | 6,8-dipropylpyridylphenoxazine-10-yl-propylsulfonate, |
| 3-methylpyridylphenoxazine-10-yl-propylsulfonate, | 3-butylpyridylphenoxazine-10-yl-propylsulfonate, |
| 6-methylpyridylphenoxazine-10-yl-propylsulfonate, | 6-butylpyridylphenoxazine-10-yl-propylsulfonate, |
| 8-methylpyridylphenoxazine-10-yl-propylsulfonate, | 8-butylpyridylphenoxazine-10-yl-propylsulfonate, |
| 3,6-dimethylpyridylphenoxazine-10-yl-propylsulfonate, | 3,6-dibutylpyridylphenoxazine-10-yl-propylsulfonate, |
| 3,8-dimethylpyridylphenoxazine-10-yl-propylsulfonate, | 3,8-dibutylpyridylphenoxazine-10-yl-propylsulfonate, |
| 6,8-dimethylpyridylphenoxazine-10-yl-propylsulfonate, | 6,8-dibutylpyridylphenoxazine-10-yl-propylsulfonate, |
| 3-ethylpyridylphenoxazine-10-yl-propylsulfonate, | 3-chloropyridylphenoxazine-10-yl-propylsulfonate, |
| 6-ethylpyridylphenoxazine-10-yl-propylsulfonate, | 6-chloropyridylphenoxazine-10-yl-propylsulfonate, |
| 8-ethylpyridylphenoxazine-10-yl-propylsulfonate, | 8-chloropyridylphenoxazine-10-yl-propylsulfonate, |
| 3,6-diethylpyridylphenoxazine-10-yl-propylsulfonate, | 3-bromopyridylphenoxazine-10-yl-propylsulfonate, |
| 3,8-diethylpyridylphenoxazine-10-yl-propylsulfonate, | 6-bromopyridylphenoxazine-10-yl-propylsulfonate, |
| 6,8-diethylpyridylphenoxazine-10-yl-propylsulfonate, | 8-bromopyridylphenoxazine-10-yl-propylsulfonate, |
| 3-propylpyridylphenoxazine-10-yl-propylsulfonate, | 6-propylpyridylphenoxazine-10-yl-propylsulfonate, |
| 6-propylpyridylphenoxazine-10-yl-propylsulfonate, | 8-propylpyridylphenoxazine-10-yl-propylsulfonate, |
| 8-propylpyridylphenoxazine-10-yl-propylsulfonate, | 3,6-dipropylpyridylphenoxazine-10-yl-propylsulfonate, |
| 3,6-dipropylpyridylphenoxazine-10-yl-propylsulfonate, | 3,8-dipropylpyridylphenoxazine-10-yl-propylsulfonate, |
| 3,8-dipropylpyridylphenoxazine-10-yl-propylsulfonate, | 6,8-dipropylpyridylphenoxazine-10-yl-propylsulfonate, |
| 6,8-dipropylpyridylphenoxazine-10-yl-propylsulfonate, | 3-butylpyridylphenoxazine-10-yl-propylsulfonate, |

-continued

| | |
|---|---|
| 3-butylpyridylphenoxazine-10-yl-propylsulfonate, | 6-butylpyridylphenoxazine-10-yl-propylsulfonate, |
| 6-butylpyridylphenoxazine-10-yl-propylsulfonate, | 8-butylpyridylphenoxazine-10-yl-propylsulfonate. |

Each of the above compounds can be a pyridylphenothiazine instead of a pyridylphenoxazine such as N-methylpyridylphenthiazine in lieu of N-methylpyridylphenoxazine.

Specific examples of the compounds represented by formula (I-d) are as follows:

| | |
|---|---|
| N-methyldipyrazinophenoxazine, | 3-butyldipyrazinophenoxazine-10-yl-propylsulfonate, |
| N-ethyldipyrazinophenoxazine, | 6-butyldipyrazinophenoxazine-10-yl-propylsulfonate, |
| N-propyldipyrazinophenoxazine, | 3,6-dibutyldipyrazinophenoxazine-10-yl-propylsulfonate, |
| sodium dipyrazinophenoxazine-10-yl-propanesulfonate, | 3-chlorodipyrazinophenoxazine-10-yl-propylsulfonate, |
| sodium dipyrazinophenoxazine-10-yl-2,4-dimethyl-1,3-butadienesulfonate, | 6-chlorodipyrazinophenoxazine-10-yl-propylsulfonate, |
| 3-methyldipyrazinophenoxazine-10-yl-propylsulfonate, | 3-bromodipyrazinophenoxazine-10-yl-propylsulfonate, |
| 6-methyldipyrazinophenoxazine-10-yl-propylsulfonate, | 6-bromodipyrazinophenoxazine-10-yl-propylsulfonate, |
| 3,6-dimethyldipyrazinophenoxazine-10-yl-propylsulfonate, | 3-butyldipyrazinophenoxazine-10-yl-propylsulfonate, |
| 3-ethyldipyrazinophenoxazine-10-yl-propylsulfonate, | 6-butyldipyrazinophenoxazine-10-yl-propylsulfonate, |
| 6-ethyldipyrazinophenoxazine-10-yl-propylsulfonate, | 3,6-dibutyldipyrazinophenoxazine-10-yl-propylsulfonate. |
| 3,6-diethyldipyrazinophenoxazine-10-yl-propylsulfonate, | |

Each of the above compounds can be a dipyrazinophenothiazine instead of a dipyrazinophenoxazine such as 3,6-diethyldipyrazinophenothiazine-10-yl-propylsulfonate in lieu of 3,6-diethyldipyrazinophenoxazine-10-yl-propyl sulfonate.

In certain instances, one or more azines are disclosed in U.S. Pat. Nos. 5,171,668, 5,445,755 and/or 6,432,662, incorporated herein by reference. Further, one or more structures disclosed as Formula I, II or III in U.S. Pat. No. 6,897,036 can also be used as azines. U.S. Pat. No. 6,897,036 is incorporated herein by reference.

In certain aspects, the one or more azines are present at a total concentration of about 0.01 mM to about 1M. In other words, if the reaction has two azines the total azine concentration combined is 0.01 mM to about 1M. In certain instances, the one or more azines are present at about 0.01 mM to about 500 mM such as 1 mM to about 100 mM or about 1, 10, 20, 30, 40, 50, 60, 70, 80, 90, or about 100 mM. In other instances, the one or more azines are present at about 0.01 mM to about 50 mM such 0.01, 0.1, 1, 5, 10, 15, 20, 25, 30, 35, 40, 45, or 50 mM.

In certain aspects, in the first part is PTA and is present at about 0.01 mM to about 5 mM (e.g, 0.7 mM) and PTAS, which is present at about 0.5 mM to about 50 mM (e.g, 40 mM).

The formulations and methods also include an oxidant. A wide variety of oxidants are suitable for use in the present invention. Suitable oxidants include, but are not limited to, a perborate or a peroxide. Suitable peroxides include hydrogen peroxide ($H_2O_2$) or urea-hydrogen peroxide (urea-$H_2O_2$). In addition, perborate can be sodium perborate ($NaBO_3$) or potassium perborate ($KBO_3$). Those of skill in the art will know of other oxidants such as other peroxides and perborates suitable for use in the present invention. In certain aspects, the oxidant is present in the second part at a concentration of about 0.1 mM to about 100 mM. In certain aspects, the oxidant is present at about 1 mM to about 20 mM such as about 1, 2, 3, 4, 5, 6, 7, 8, 9, 10, 11, 12, 13, 14, 15, 16, 17, 18, 19 or about 20 mM. In certain other aspects, sodium perborate is present at about 1 mM to about 10 mM such as about 1, 2, 3, 4, 5, 6, 7, 8, 9 or 10 mM. In certain instances, the pH of the solution is about pH 2-12 such as 2, 3, 4, 5, 6, 7, 8, 9, 10, 11 or 12.

In certain instances, the first part of the formulation further comprises a nucleophilic reagent. In one aspect, the nucleophilic reagent comprises at least one five- or at least one six-membered ring, which is an aryl group or heteroaryl group, wherein the at least one five- or the at least one six-membered ring can be a fused aryl group or fused heteroaryl group. In certain aspects, the nucleophilic reagent is present in the first part at about 0.01 mM to about 1 M. In other aspects, the nucleophilic reagent is present at about 0.1 to about 100 mM or about 10, 20, 30, 40, 50, 60, 70, 80, 90, or about 100 mM. In certain aspects, the nucleophilic reagent is present at about 10 mM to about 50 mM.

In certain instances, the nucleophilic reagent comprises an imidazoyl, a pyrazolyl, a triazolyl, a pyridyl, a phenyl, or a phenoyl moiety, which moiety is optionally fused to another ring.

In certain instances, the nucleophilic reagent is selected from the group of 4-(1,2,4-triazol-1-yl)phenol, 2-(1H-imidazol-2-yl)pyridine (2-IP), dimethylamino pyridine (DMAP) and 4-morpholinopyridine (MORP).

In one preferred aspect, the nucleophilic reagent is MORP.

A wide variety of phenols are nucleophilic reagents suitable for use in the present invention. In one aspect, the phenol is selected from the group of 4-indophenol, 4-iodophenol, 4-(3-thienyl)phenol, 4-(1-pyrrolyl)phenol, 4-(4- tolyl)phenol, 4-carboxy-4-hydroxybiphenol (BIPCA), 4-bromo-4-hydroxyphenol, p-Coumaric acid or a combination thereof. In a preferred aspect, the phenol is 4-carboxy-4-hydroxybiphenol (BIPCA).

Other optional additives include, but are not limited to, (hydrazine-1,2-diylidene)bis(3-ethyl-2,3-dihydrobenzo[d]thiazole-6-sulfonate) (ABTS), 3-indole acetic acid (IAA), and tetramethylbenzidine (TMB).

In one aspect, the nucleophilic reagent is a compound of formula (II):

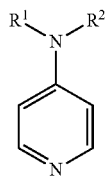

wherein: $R^1$ and $R^2$ represent both or each separately, hydrogen, methyl, ethyl, propyl, butyl and isopropyl, or $R^1$ and $R^2$ together represent —$(CH_2)_4$— thus forming a pyrrolidone ring with the nitrogen atom, or $R^1$ and $R^2$ together represent —$(CH_2)_5$— thus forming a piperidine ring with the nitrogen atom, or $R^1$ and $R^2$ together represent —$(CH_2)_2$—$CHCH_3$—$(CH_2)_2$— thus forming a 4-methylpiperidine ring with the nitrogen atom, or $R^1$ and $R^2$ together represent —$(CH_2)_2$—O—$(CH_2)_2$— thus forming a morpholine ring with the nitrogen atom, or $R^1$ and $R^2$ together represent —$(CHCH_3)$—$CHCH(CHCH_3)$— thus forming a 2,5-dimethyl-2,5-dihydro-1H-pyrrole ring with the nitrogen atom.

In another aspect, the nucleophilic reagent is a compound of formula (III):

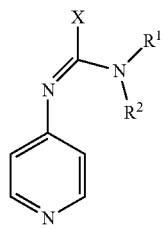

where: X represents hydrogen, methyl, ethyl, propyl, butyl or isopropyl, while $R^1$ and $R^2$ represent both or each separately, hydrogen, methyl, ethyl, propyl, butyl and isopropyl, or X represents $NH_2$, or $N(methyl)_2$, or $N(ethyl)_2$, or $N(propyl)_2$, or $N(isopropyl)_2$, or $N(butyl)_2$, while $R^1$ and $R^2$ represent both or each separately, hydrogen, methyl, ethyl, propyl, isopropyl, or butyl.

In certain aspects, the first part of the formulation further comprises a buffer. The buffer maintains the pH of the first part between a pH of about 3 to about 12, or about 3-6, 6-8, 6-9, 6-10, 6-11, 7-9, 7-10, 7-11, 7-12, 8-10, 8-11, 8-12, 9-10, 9-11, 9-12, 10-11, 10-12, 6, 7, 8, 9, 10, 11, or a pH of about 12. In one aspect, the buffer of the first part is a Tris buffer or citric buffer. The Tris or citric acid buffer can have a concentration of about 25 mM to about 1000 mM, such as about 25, 50, 100, 200, 300, 400, 500, 600, 700, 800, 900 or 1000 mM (1.0 M).

In certain aspects, the second part of the formulation further comprises a buffer. In a preferred aspect, the buffer of the second part has a pH of about 3 to about 9.5, such as about 3, 4, 5, 6, 7, 3-5, 3-6, 3-7, 4-6, 4-7, 5-6, 5-7 or 7-9.5.

In certain aspects, the buffer of the second part is sodium acetate. The sodium acetate buffer can have a concentration of about 1 mM to about 500 mM such about 10, 20, 30, 40, 50, 60, 70, 80, 90, 100, 200, 300, 40 or about 500 mM.

In still other aspects, the first part further comprises a buffer and a solubilizing agent. The solubilizing agents can be one or more water soluble polymers or a mixture of a polymer with a surfactant such as polyethylene glycol, Triton X-100 or a mixture thereof. The solubilizing agent increases one or more azines solubility from 0.1 µM to 5 mM. The solubilizing agent is typically present from about 0.1% to about 20% w/v such as about 1% to 10% w/v or 1, 2, 3, 4, 5, 6, 7, 8, 9 or 10% w/v.

In certain instances, the solubilizing agent can be synthetic or natural water soluble polymers such as dextran sulfate, poly(ethylene glycol) (PEG), alginic acid, a copolymer of methyl vinyl ether and maleic anhydride, carrageenan, polyvinylpyrrolidone such as polyvinylpyrrolidone 40 KDa, ethylene glycol, and mixtures thereof.

In certain instances, the solubilizing agent is selected from PEG 200, PEG 400, PEG 1450, PEG 3350, PEG 4000, PEG 6000, PEG 8000 and a mixture thereof.

In certain instances, the solubilizing agent is a surfactant. Various surfactants are suitable for the present invention. In a preferred aspect, the surfactant is a nonionic surfactant.

In certain instances, the solubilizing agent is selected from the group consisting of polysorbate 80, polyoxyethylene (20), sorbitan monooleate, Tween-20, Tween 80, poloxamer, Triton X-100, Triton X-114, NP-40, Brij-35, Brij-58, octyl-β-glucoside, octyl-beta-thioglucopyranoside (OTG), SDS, CHAPS, and CHAPSO.

In certain instances, the solubilizing agent is substantially free or free of any oxidizing impurities (i.e., substantially free or free of oxidant(s)). If present, an oxidant impurity is no greater than about 0.0-0.5% w/w, such as 0.001, 0.002, 0.003, 0.004, 0.005, 0.006, 0.007, 0.008, 0.009, or less than 0.01, or 0.1, or 0.2, or 0.3. or 0.4, or less than 0.5% w/w.

The absence of oxidizing impurities in the first part of the formulation increases the shelf-life of the solution. The formulated solution substantially free of oxidants is stable at room temperature for 1, 3, 6, 9, 12, 15, 18, 21, 24 months, about 1 year, 18 months, 2 years or even longer.

In certain aspects, the present invention provides methods using a catalytic reagent such as a peroxidase. Various peroxidase enzymes can be used. Preferably, horseradish peroxidase is used. Typical concentrations are in the range of 0.001 pM to 1 nM or more. It will often be convenient to perform multiple assays in parallel in individual wells of a multiwell plate. In one assay format, all the reagents are present in solution.

In other aspects, the present invention provides methods using a catalytic reagent that functions similarly to a peroxidase ("peroxidase-like activity"), such as horseradish peroxidase (HRP), transition metal complexes (such as Cu, Ni, Fe and Mn complexes), nanoparticles (such as Pd nanoparticles) or cytochrome C, but is not an enzyme. The catalytic agent can be a phthalocyanine metal catalyst and is disclosed in U.S. patent application Ser. No. 14/262,659, filed Apr. 25, 2014, (US 2015-0267108) the disclosure of which is hereby incorporated by reference.

In general, the working solution is aqueous (substantially aqueous), although in order to achieve solubility of a particular substrate, it may be necessary to include organic solvents such as dimethyl sulfoxide (DMSO) or alcohols. The working solution can generally be used at room temperature or a temperature of about 10 to about 50° C., such as about 10, 15, 20, 25, 30, 35, 37, 40, 45, or 50° C.

Preferably, the reaction temperature is about 20, 21, 22, 23, 24, 25, 26, 27, 28, 29 or 30° C.

It is believed that an azine derivative is generated through a series of radical coupling reactions (see, Scheme 1, FIG. 1). Without being bound by any particular theory, it is believed that formation of a colorgenic and or a fluorogenic species is an azinium blue compound. For example, A and B each represent any 5- or 6-membered substituted or unsubstituted aromatic ring; C is a nitrogen containing 6-membered ring; X is oxygen, nitrogen or sulfur; D is at least one ring that extents the conjugation; and Y is carbon, nitrogen or another atom that extends the conjugation.

Quite advantageously, the product having a D ring provides the means to detect proteins and peroxidase activity visually, digitally, rapidly (e.g, in less than 5 minutes) using and with high sensitivity (e.g, 2-4 fold higher than available ECL chemiluminescent substrates) using suitable membranes and solution based assays.

Scheme 2 illustrates yet another aspect of the present invention. As shown therein, the PTA substrate is rapidly oxidized by an oxidant in the presence of a peroxidase enzyme or peroxidase-like compound. In this embodiment, the radical cation undergoes dimerization or couples with other nucleophilic reagents. The azinium dimer, which is chromogenic is visible as a blue color and is detectable by near infrared fluorescence properties.

Scheme 3 illustrates still yet another aspect of the present invention. In certain aspects, the azine can be used to increase the oxidation rate and production of more radical cations of azines by a synergistic effect. Typically, the azine can be a water soluble azine such as PTA derivatives or a compound of Formula Ia, Ib, Ic, Id or mixtures thereof. In one aspect, N-substituted phenothiazines, such as 3-(10'-phenothiazinyl)propane-1-sulfonate (PTAS) are used to generate abundance of radical cations in peroxidase-catalyzed reaction system.

In certain aspects, the one or more azines can be at least two azines having different solubilities. In certain assay conditions, the at least two azines are mixed. In one aspect, the solubility of the first azine in aqueous solution is lower than the second azine. For example, the solubility of the first azine is 10 to 10,000 times more soluble than the second azine in an aqueous solution. In other aspects, the first azine may be from 10 to 8000, or from 100 to 5000, or from 500 to 2000 times more soluble than the second azine.

The molar ratio of mixed azines in a solution particularly, PTA/PTAS is from 1:10 1:50; or a ratio of 1:100.

In certain aspects, the nucleophilic reagent such as a compound of Formula II or III is used for producing more colored and fluorescent compounds via nucleophilic attack of the radical cation. Without being bound by any particular theory, Scheme 4 is one illustration of such a reaction. This type of nucleophilic reagent belongs to five or six membered nitrogen heteroaromatic ring compounds, such as pyridines and its derivatives; N-azoles and the like.

In one aspect, a buffer system is used for increasing the solubility of an azine and for making colored and fluorescent azinium compounds. In one aspect, the solvent system comprises a lower alkanol (e.g, $C_2$ alkanol) dimethyl sulfoxide, a solubility enhancer (e.g a nonionic surfactant) and an aqueous buffer.

The formulations, methods, systems and kits are useful in connection with the detection of analytes of all types (e.g, biological molecules, organic molecules, natural or synthetic molecules). The invention is particularly applicable to detection of proteins and nucleic acids using all types of membrane-based assays by techniques such as Western blotting, Dot blotting, Southern blotting, and Northern blotting. Furthermore, the present invention is particularly applicable to the detection of analytes using all types of solution-based, luminometric assays, such as ELISAs (Enzyme Linked Immunoabsorbent Assays), bead assays, and the like.

Figure 6A:
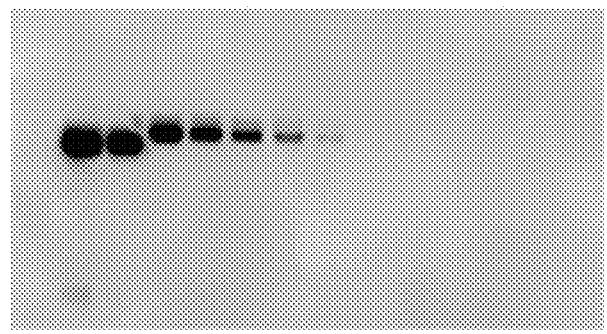
FIGS. 6A-6B show at least 4-fold increase in sensitivity (at least 4-fold) of the PTA substrate compared to SuperSignal™ West Femto Substrate.
Figure 6B:
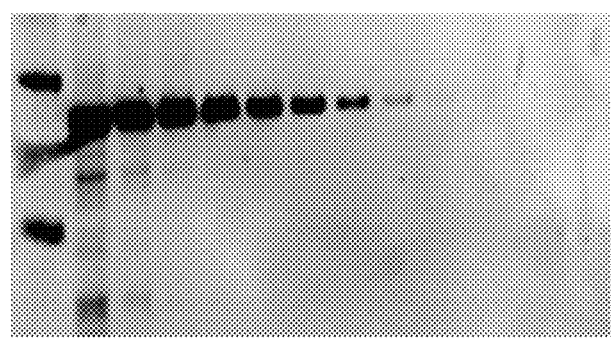
Figure 7A:
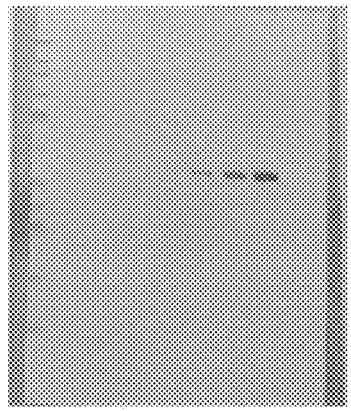
FIGS. 7A-7G shows that the visual limit of detection (LOD) comparison; chromogenic PTA substrate shows 2-fold higher sensitivity compared to the 1-Step TMB-Blotting Substrate Solution (Thermo Fisher).
Figure 7B:
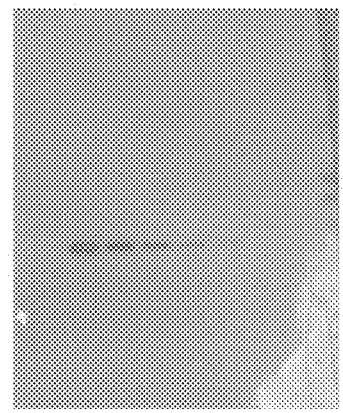
Figure 7C:
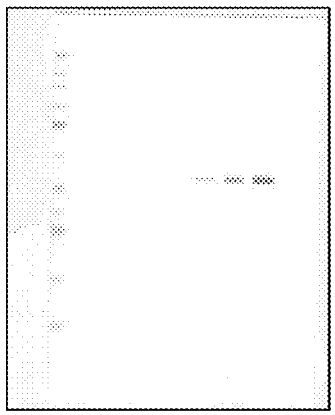
Figure 7D:
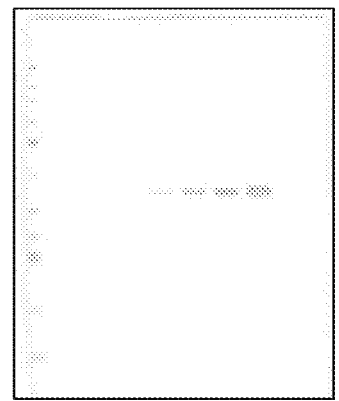
Figure 7E:
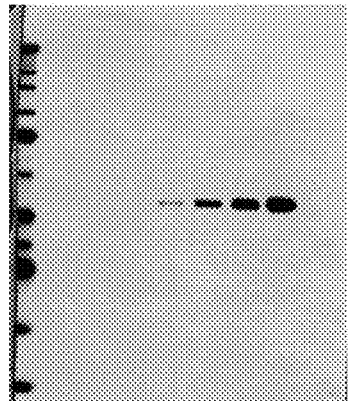
Figure 7F:
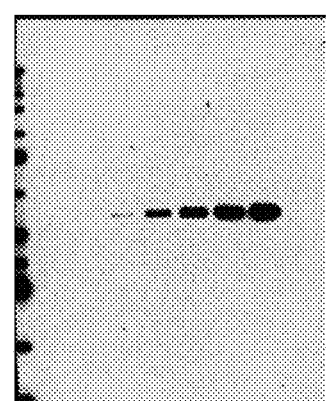
Figure 7G:
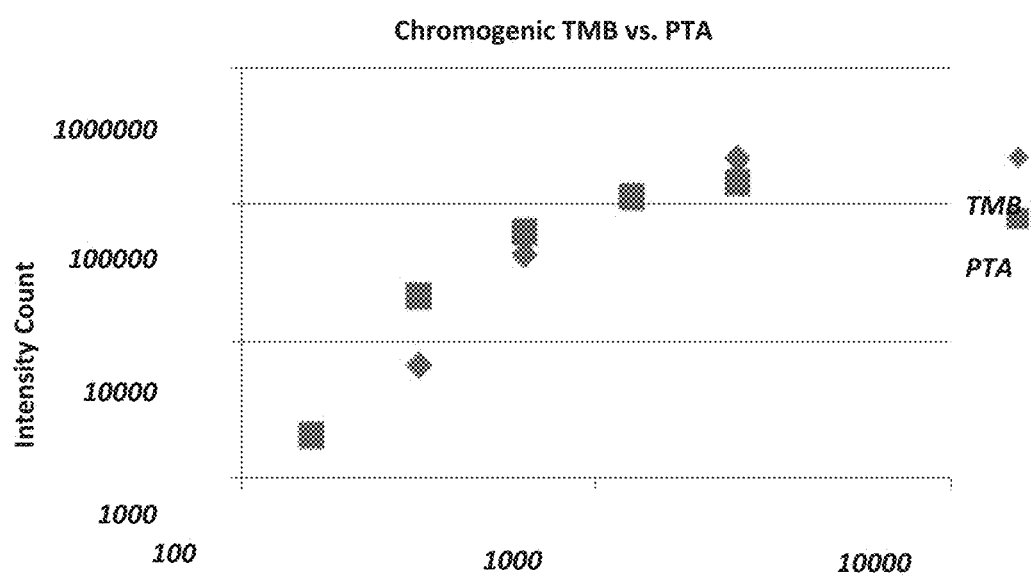
Figure 8A:
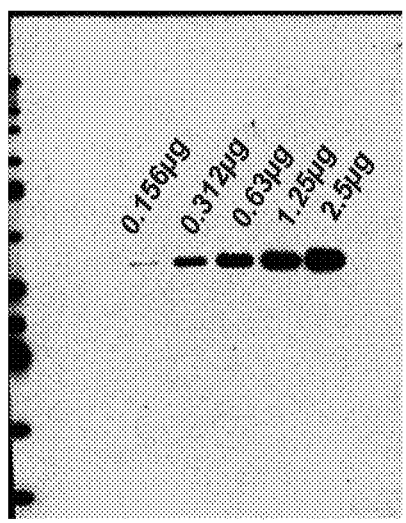
FIGS. 8A-B show the same sensitivity of analytes on Western blots treated with the chromogenic PTA substrate (FIG. 8A, inverted picture by Image Studio® software) and SuperSignal™ West Femto Substrate (FIG. 8B, Chemisignal obtained by Odyssey Fc).
Figure 8B:
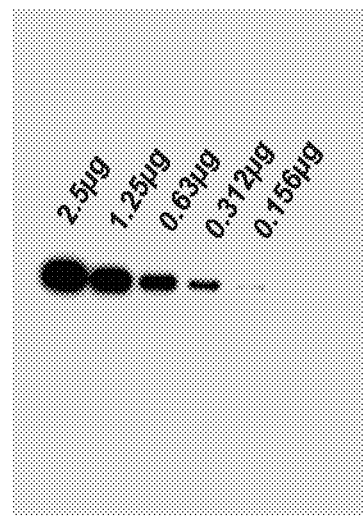

In certain aspects, the systems, formulations and kits of the invention are able to detect biomolecules on Western Blot and ELISA by colorimetric and fluorescence. The fluorogenic detection method gives better sensitivity than ultrasensitive enhanced chemiluminescence (ECL) substrates (FIGS. 6A and 6B). The colormetric method is quick and easy to visualize the color appearance upon contacting with analytes. The use of this system and methods gives sensitivity enhancement as compared to TMB chromogenic substrate (FIG. 7). For a high abundance protein, the visual LOD (by naked eye) is comparable to LOD measured by most sensitive chemiluminescence substrate (FIG. 8B).

Figure 11A:
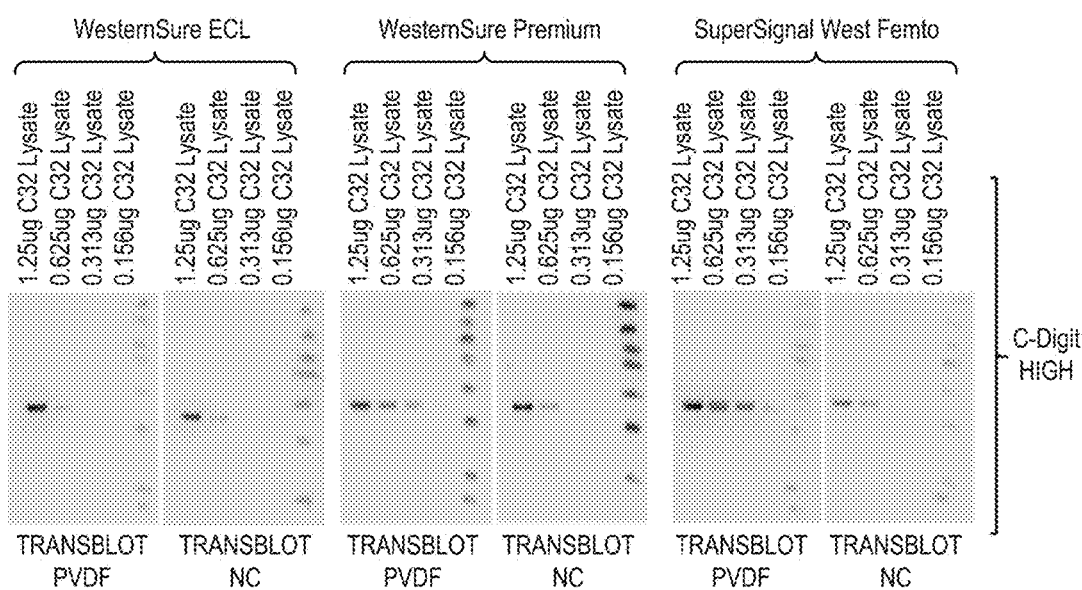
FIGS. 11A-B show detection of Actin on Western blots using three chemiluminescence substrates (FIG. 11A) and reprobing the Actin on the same blots using chemifluorescence substrate (FIG. 11B). The sensitivity of a chemifluorescent substrate is 2-4-fold higher depending on which ECL substrate used.
Figure 11B:
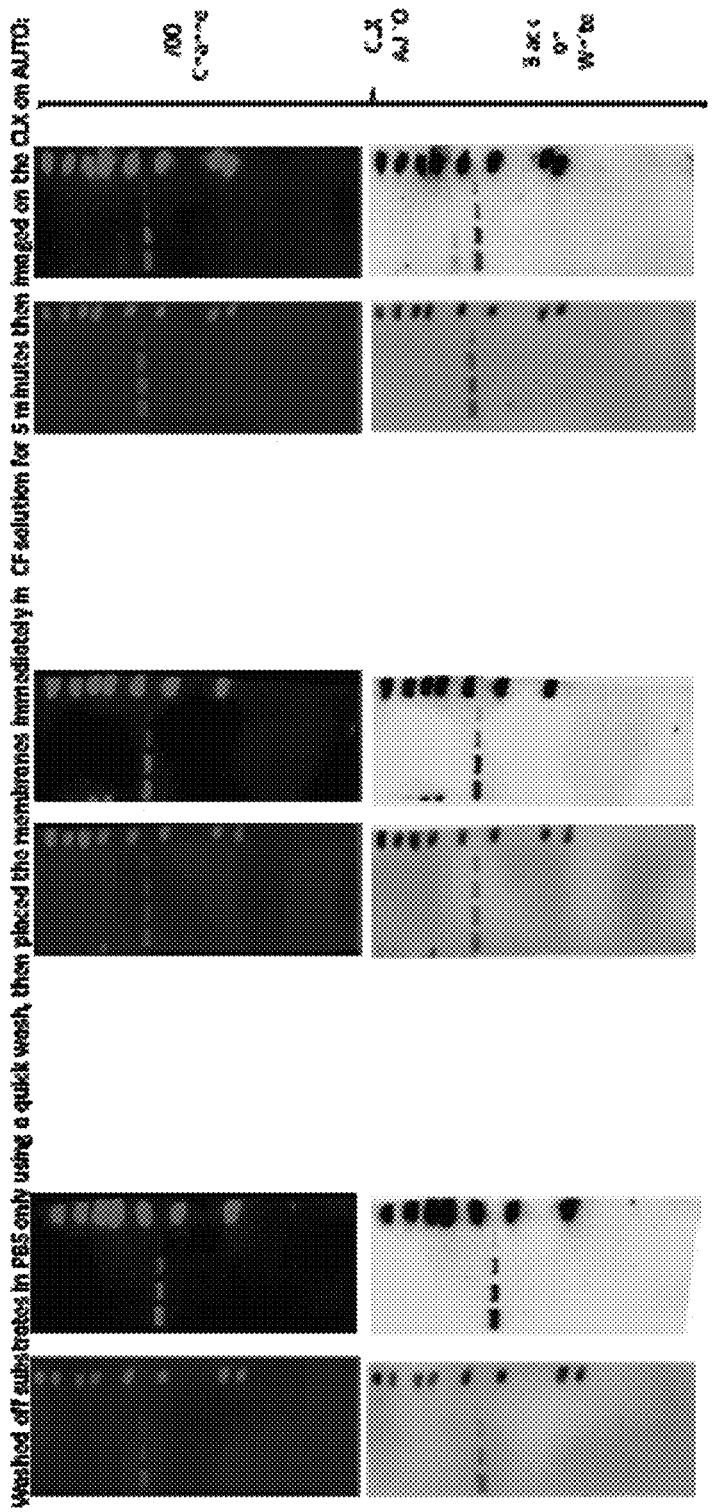

In certain aspects, the kit can be used for reprobing biomolecules after chemiluminescence detection on Western blot. Without stripping, treating the blot with a kit of the present invention produces 2~4 times higher visual LOD and the signal will not fade. (FIGS. 11A-B).

In certain instances, the formulations, methods and kits of the present invention are used in Enzyme Linked Immunosorbent Assays (ELISAs), which utilize an enzyme label for the detection of proteins. Typically, a specific antibody is passively absorbed to a plate. The nonspecific sites are blocked with a protein solution which has no active part in the specific immunochemical reaction of a particular assay. A specific protein of interest is captured by the antibody on the surface and then detected by another antibody with an enzyme label. The enzyme label is reacted with a formulation of the present invention and detected.

In a Western Blot application, a protein(s) is detected by first separating protein samples electrophoretically on for example, a SDS polyacrylamide gel. The proteins are then transferred electrophoretically to a membrane such as nitrocellulose or PVDF. The nonspecific sites are blocked with a protein solution that has no active part in the specific immunochemical reaction of a particular assay. A specific protein of interest is detected then by the addition of an antibody made against the protein. After a wash step to remove any unbound antibody, a peroxidase labeled antibody is added that will react with the primary antibody. The unbound enzyme labeled antibody is removed by a series of wash steps. The membrane is then exposed to a formulation of the present invention to produce color and near infrared fluorescence.

In a Dot Blot, proteins are directly applied to a membrane and detected with a previously described antibody system.

In a Southern blot, DNA is detected by first separating the DNA sample electrophoretically on an agarose gel. The DNA is then transferred to a membrane such as charge-modified nylon. The DNA is then fixed by irradiation or baking. The membrane is then blocked with a prehybridization buffer to prevent any nonspecific binding of a DNA probe. The DNA probe coupled to a detectable label such as biotin is then added to the membrane and is allowed to incubate for several hours at 50° C. or higher. The blots then undergo a series of stringency washes to remove any nonspecific hybridized probe from the DNA target while maximizing target/probe interactions. The blots are blocked again to prevent any nonspecific binding of the enzyme labeled probe. A peroxidase labeled conjugate such as streptavidin peroxidase is added to the membrane. The membrane is washed to remove any unbound label. The membrane is then exposed to a formulation of the present invention to produce color and fluorescence.

In a Southern blot, RNA is detected by separating RNA samples and detecting with a DNA or RNA probe using a method similar to the Western Blot application. Care must be taken to remove all ribonucleases which can interfere and destroy the target.

The formulations and methods provide a high degree of near infrared (near IR) fluorescence, which develops rapidly. The intense fluorescence persists for a longer period of time compared to other systems. Thus, by using the methods of the present invention, rapid development of high intensity fluorescence is achieved and the fluorescence is of an extended duration. Moreover, by combining the features of high light output with extended duration, unprecedented levels of sensitivity are achieved in many assay systems.

The present invention is also useful in applications for visual and high sensitivity assays using colormetric methods. The color image can be converted to digital images by Image studio software, therefore, a semi-quantification can be obtained.

The oxidized one or more azines have fluorogenic emissions that can be measured between about 320 nm and about 950 nm or about 350 nm and about 950 nm. In addition, their chromogenic activity is measured between about 300 nm and about 900 nm.

In certain instances, their emission wavelengths is in the NIR spectrum, between 550-850 nm or about 600-825 nm or about 650 and 800 nm. After excitation, the near infared fluoresence emission and intensity of the the oxidized substrate can be detected using a fluorometer or fluoresence imager. Suitable systems for detection include the LI-COR Odyssey Systems including Odyssey CLx, Odyssey Sa and Odyssey Fc. In addition to the foregoing, a plate reader or spectrophotometer can be used and the amount of absorbance can be measured.

III. Examples

Example 1 describes exemplary embodiments of a near-infrared fluorogenic and chromogenic substrate.

The phenothiazine (PTA) substrate can be rapidly oxidized by an oxidant and in the presence of peroxidase enzyme. Also, the concentrated radical cation of the reaction undergoes self-dimerization or couples with other nucleophilic reagents to form an azinium compound. This azinium compound possesses a blue color and near-infrared fluorescence properties.

Figure 5B:
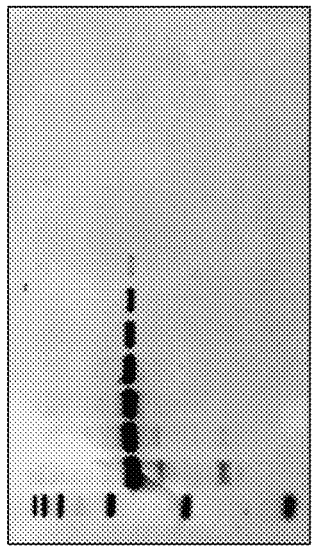
FIGS. 5A-D provide a detection comparison between SuperSignal™ Femto chemiluminescence substrate and the near-infrared fluorogenic substrate formulated at three substrate concentrations (i.e., 10H-phenothiazine (PTA), which is a fluorogenic and chromogenic substrate).
Figure 5D:
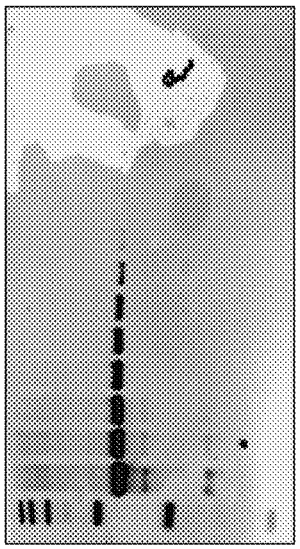
Figure 5A:
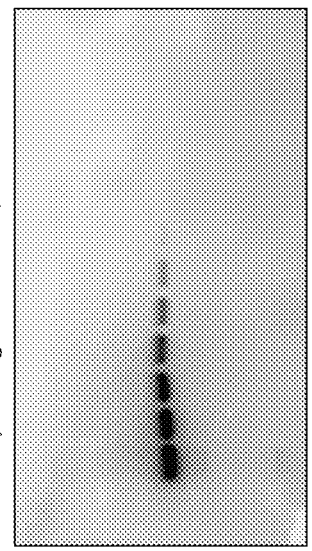
Figure 5C:

A series of tests were performed to determine the optimal concentration of PTA in the detection method. Western blot analysis was performed on cell lysates generated from the C32 cell line that expresses high levels of Erk protein. The lysates were processed according to standard western blotting protocols. Briefly, Erk protein was detected using a primary antibody against Erk (an anti-Erk monoclonal antibody) and an HRP-conjugated secondary antibody (goat anti-mouse IgG antibody). Different concentrations of the PTA substrate were compared by visualization of color formation and detection of protein bands. The limit of detection (LOD) was measured by chemifluorescence signal and compared to the LOD using Thermo Scientific™ Super-Signal™ West Femto Substrate. The data shows that the formulation containing 0.35 mM PTA has the highest sensitivity in working solution. FIG. 5 illustrates the comparison and effect of PTA concentration on LOD of Erk protein in C32 cell lysates. FIG. 5A shows the chemiluminescent signal from SuperSignal™ West Femto Substrate. FIGS. 5B-5D shows the fluorescence signal at 700 nm with different concentrations of PTA ranging from 0.65 mM PTA to 0.15 mM PTA in working solution.

The optimal concentrations of the cation radical enhancer, nucleophilic reagent, solvent system and oxidant in the formulation were also tested. Water soluble azine, particularly 3-(10'-phenothiazinyl)propane-1-sulfonate (PTAS) was tested at various concentrations from 2 to 30 mM in a working solution. The effects were evaluated using the rate (speed) of visualization and the number of colored band on western blot. The preferred concentration of PTAS was 18 mM. Other water soluble and N-substituted PTA derivatives can also be used in place of PTAS or in combination thereof. The nucleophilic reagent serves as a co-substrate in the detection solution. The nucleophilic reagent can include five or six membered nitrogen heteroaromatic ring compounds. MORP at concentrations from 0 to 20 mM was tested in the formulation. Based on the number of colored bands detected, the preferred concentration was 15 mM MORP in the working solution.

Next, the solvent system for phenothiazine (PTA) was tested. Although, PTA has low solubility (0 μM in water), different compounds such as water soluble polymers and surfactants enhance the solubility of PTA in a suitable biological assay buffer. The solubility of PTA with polymers was tested by precipitate visualization and by HPLC of fresh and stored samples. Table 1 provides a comparison of polymers that include PTA solubility in an assay buffer, such as Tris buffer, pH 9.5.

TABLE 1

Comparison of Detergents, Polymers, etc. on PTA solubility in assay buffer

| Compound | Concentration (w/v) | Appearance of solution | Appearance of PTA solution after overnight storage at room temperature |
| --- | --- | --- | --- |
| No solubilizer added | | cloudy | Precipitate, 0.15 μM |
| Dextran Sulfate, 200 KDa | 2.4% | cloudy | Precipitate, 0.5 mM |
| Brijig 35 | 4% | cloudy | Precipitate, 0.5 mM |
| Alginic acid | 4% | cloudy | Precipitate, 0.5 mM |
| Methyl vinyl ether/maleic anhydride | 4% | cloudy | Precipitate, 0.5 mM |
| Carrageenna | 4% | | Precipitate, 0.5 mM |
| Polyvinyl-pyrrolidone (PVP) 40 KDa | 2%~6% | clear | 0.25-1.5 mM, soluble |
| PEG 8000 | 5% | cloudy | Precipitate, 0.5 mM |
| PEG 8000 + Triton X-100 | 5% PEG8000 + 0.2% Triton X-100 | soluble | 0.25-1 mM, soluble |
| Ethylene Glycol (EG) | 6% | cloudy | Precipitation, 0.5 mM |
| Ethylene Glycol (EG) + Triton X-100 | 6% EG + 0.2% Triton X-100 | cloudy | Precipitation, 0.5 mM |

The data clearly shows that PVP 400 and a mixture of PEG-8000 and Triton X-100 are both solubilizers that can enhance the solubility of PTA in assay buffer. These polymers can be used to dissolve PTA and other azines that have low solubility in standard assay buffers, e.g, Tris buffer, pH 8.0-10.5, or pH 8.0-9.6.

Stable oxidants that are compatible with HRP-azine system are tested. Sodium perborate ($NaBO_3$), Urea-$H_2O_2$ and stabilized $H_2O_2$ at certain concentrations accelerated azine oxidization and formation of colored and fluorescent compounds.

The exemplary formulation of the detection solution tested comprises two concentrated solutions: Solution A (a first part) and Solution B (a second part). Solution A comprises 36 mM PTAS, 0.7 mM PTA, 30 mM MORP, 6% PVP40, 200 mM Tris, 3% ethanol and 6% DMSO, pH 9.5. Solution B comprises 7.5 mM $NaBO_3$, 50 mM NaOAc/ HOAc (pH 4.8). The working detection solution was made by using equal volumes of Solution A and Solution B, with a final pH of 8.90.

Three commercial solubilizers were dissolved in water and monitored by HPLC at 280 nm. FIG. 12A shows the level of oxidation impurities in a solubilizer. Source 2 has the highest level of impurities. In a preferred formulation of solution A, HPLC and LC-MS were used to measure and identify the oxidized azines. As can be seen from FIGS. 12 B and C, the level of oxidation impurities in a solubilizer strongly correlates with the amount of oxidized PTAS and PTA and these are also time-dependent. The more oxidation impurity, the more PTAS and PTA are oxidized, and for example, solubilizer from source 2 yields the highest degree of azine oxidation. Such oxidized azines may not only produce high background in peroxidase based chemifluorescence assays, but also inhibit peroxidase activities in all kinds of assay formats.

Example 2 shows the performance of the exemplary detection solution described above to detect high abundance proteins by western blotting.

In this experiment Erk protein was detected in C32 cell lysates using a 1:1000 dilution of a monoclonal antibody directed to Erk. 10 μg to 1.3 ng of protein was run on each gel. The membrane was blocked with 5% milk. A secondary antibody of HRP labeled goat anti-mouse IgG antibody was used at a 1:25,000 or 1:5000 dilution. Identical western blots were generated in order to directly compare the performance of the inventive formulation comprising PTA and a commercially available chemiluminescent substrate. Near-infrared fluorescence from PTA treated blot was detected using the Odyssey® CLx system set at the 700 channel. Chemiluminescence from the control blot was detected using the Odyssey® Fc imaging system set at the chemiluminescence channel.

FIGS. 6A-6B show increased sensitivity (at least 4-fold) of the inventive formulation comprising PTA compared to SuperSignal™ West Femto Substrate. FIG. 6A shows 7 protein bands on the membrane treated with SuperSignal™ West Femto Substrate. FIG. 6B shows 9 protein bands on the membrane treated with the inventive formulation comprising PTA.

Another exemplary formulation comprises two solutions. Solution A comprises 20 one azine compound, i.e. 3,7-bis (dimethylamino)-10H-phenothiazin-10-yl((phenyl)methanone (BLMB), 4% dextran sulfate, 60 μM 4-(dimethylamino)pyridine (DMAP), 400 μM 6-hydroxy-2-naphthoic acid (HNA) in 200 mM citric buffer, pH 5.3. Solution B comprises 5 mM $NaBO_3$ in 50 mM HOAc (pH 4.8). The working detection solution is made by using equal volumes of Solution A and Solution B, with a final pH of 5.0. A 2~4 fold enhancement in sensitivity is also observed as compared to SuperSignal West Femto Chemiluminescence Substrate (Thermo).

Another example is a phenoxazine based formulation. This formulation comprises solutions A and B. Solution A comprises 1 mM phenoxazine (POA), 30 mM 3-(10H-phenoxazin-10-yl)-1-propanesulfonic acid, 10 mM 1,2,3-triazole, 200 mM Tris buffer (pH 9.5). Solution B comprises stabilized $H_2O_2$ (pH 8.5). The working detection solution is made by using equal volumes of Solution A and Solution B, with a final pH of 8.5. A pink colored band and chemifluorescence at 600 nm is used to determine the amount of analytes in biological samples.

Figure 3:
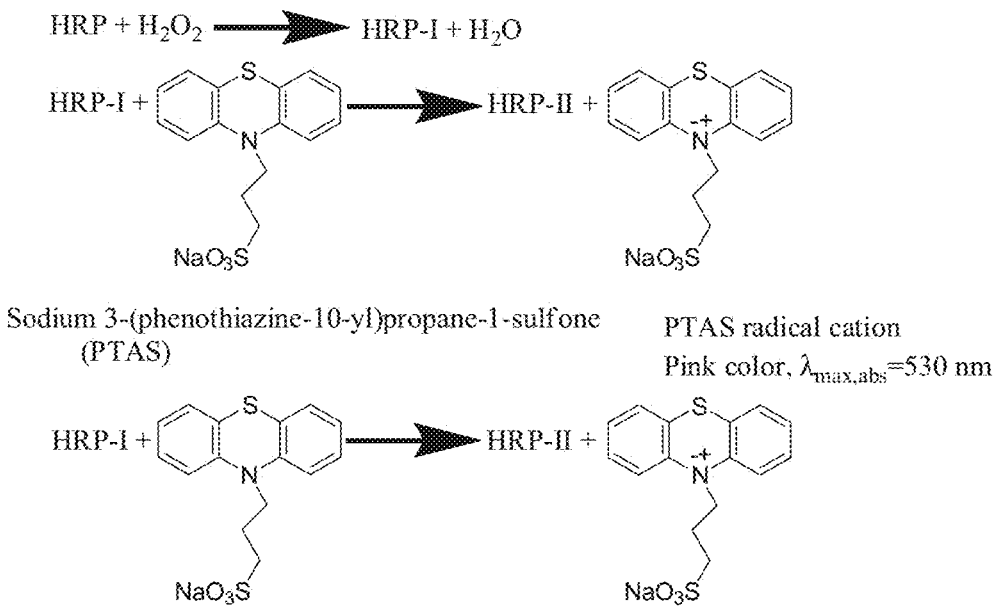
FIG. 3 illustrates Scheme 3, which shows one embodiment of the present invention.
Figure 4:
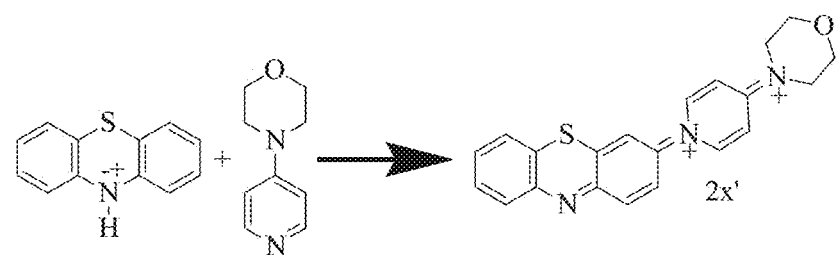
FIG. 4 illustrates Scheme 4, which shows one embodiment of the present invention.

The chromogenic performance of the exemplary detection solution was also tested. After the addition of the substrate, colored bands rapidly formed and images of the bands were captured by digital camera, e.g, iphone, and digital scanner. The quantification of the banding pattern was performed by inverting the images and quantitating using Odyssey® software. FIGS. 7A-7G shows that the visual LOD is 2-fold higher for the PTA substrate compared to the 1-Step TMB-Blotting Substrate Solution (Thermo Fisher). FIG. 7A shows a digital image of the TMB substrate blot and FIG. 7B shows a digital image of the PTA substrate blot. FIG. 7C shows a scanner image of the TMB substrate blot and FIG. 3D shows a scanner image of the PTA substrate blot. FIG. 7E shows an inverted image of the TMB substrate blot and FIG. 7F shows an inverted image of the PTA substrate blot. FIG. 7G represents a plot of the intensity of chromogenic TMB substrate versus chromogenic PTA substrate. The data shows that the PTA substrate is 2-fold more sensitive compared to the TMB substrate (TMB are diamonds). Similar results were seen with SuperSignal™ West Femto Substrate (FIGS. 8A-B).

Example 3 shows the performance of the exemplary detection solution described above to detect very low abundance proteins by western blotting.

The sensitivity of the inventive formulation comprising PTA was compared to that of the SuperSignal™ West Pico Chemiluminescent Substrate.

In this series of experiments estrogen receptor protein was detected in MCF7 cell lysates using a 1:1000 dilution of a rabbit antibody directed to the estrogen receptor. The PVDF membrane was blocked with 5% milk. A secondary antibody of HRP labeled goat anti-rabbit IgG antibody was used at a 1:5000 dilution. Identical western blots were generated produced in order to directly compare the performance of the inventive formulation comprising PTA and a commercially available chemiluminescent substrate.

Figure 9A:
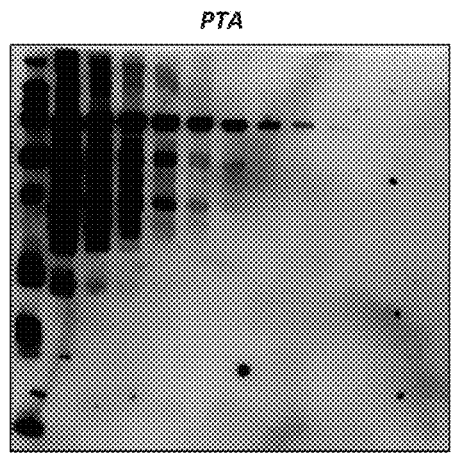
FIGS. 9A-9C show detection of low abundance analytes on Western blots treated with the fluorogenic PTA substrate (FIG. 9A, near-infrared fluorescence image) or SuperSignal™ West Pico Substrate (FIG. 9B, image recorded on digital instrument Odyssey Fc and 9C, image recorded on blue Film).
Figure 9B:
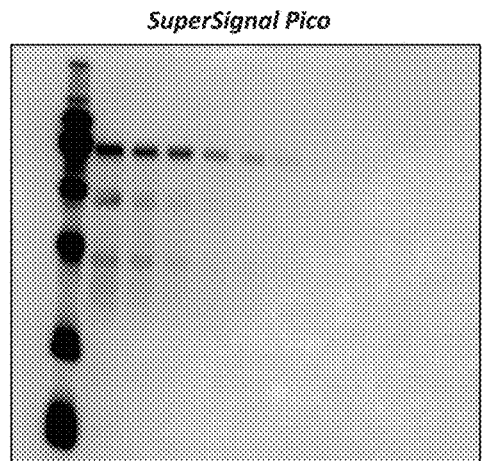
Figure 9C:
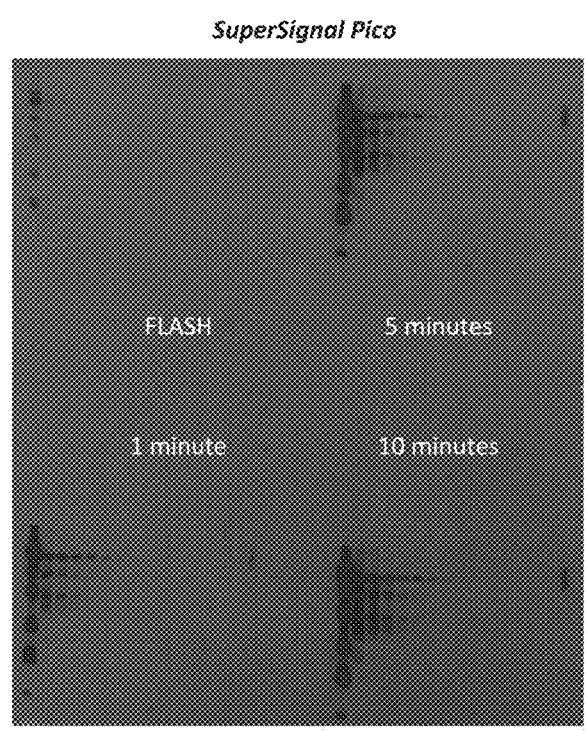

Near-infrared fluorescence from the inventive formulation comprising PTA treated blot was detected using the Odyssey® CLx system set at the 700 channel. The fluorescence detection method was compared to chemiluminescence detection methods that utilize traditional film or a digital detection system, e.g, the Odyssey® Fc. FIGS. 9A-9C show that the sensitivity of detection was superior for the inventive formulation comprising PTA (FIG. 9A, 9 bands), compared to the SuperSignal™ West Pico Chemiluminescent Substrate with an Odyssey Fc digital imager (FIG. 9B, 6 bands) or conventional autoradiographic film (FIG. 9C). In FIG. 9A, 9 bands are detected by chemifluorescence method and only 6 bands are detected by chemiluminescence (FIG. 9B, Odyssey Fc chemi-channel). After a 10 minute exposure, 8 protein bands were visible on the film. Similar to the results for detecting high abundance proteins, the inventive formulation comprising PTA is more sensitive than the SuperSignal™ West Pico Substrate.

Figure 10A:
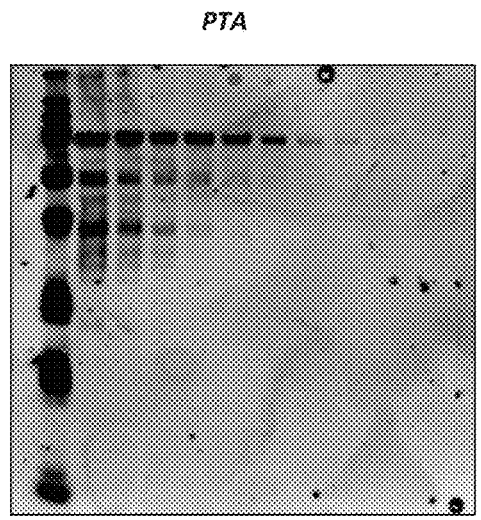
FIGS. 10A-10D show detection of low abundance analytes on Western blots treated with the fluorogenic PTA substrate (FIG. 10A) or SuperSignal™ West Femto Substrate (FIG. 10B, chemi-signal on Odyssey Fc, 10C and 10D on film).
Figure 10B:
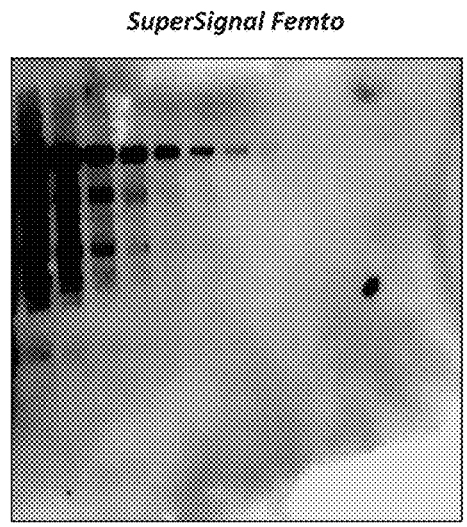
Figure 10C:
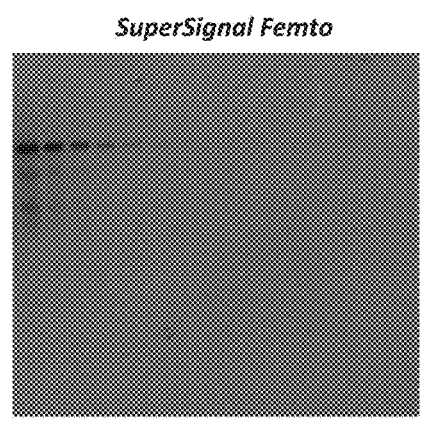
Figure 10D:
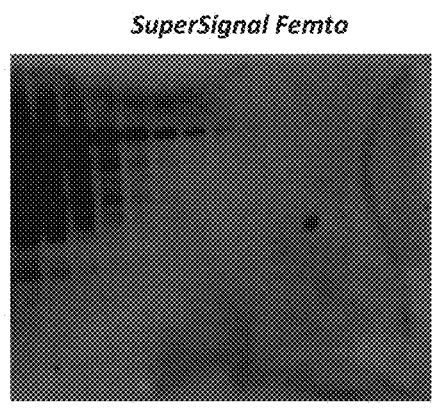

The sensitive of the chemifluorescence substrate was compared to the SuperSignal™ West Femto Substrate using the same western blotting experiments described above. FIGS. 10A-10C show that the inventive formulation comprising PTA (FIG. 10A) is equally as sensitive as SuperSignal™ West Femto Chemiluminescent Substrate with a digital imager (FIG. 10B) or conventional autoradiographic film (FIG. 10C).

The use of a chemifluorescence substrate kit can re-probe biomolecules on Western Blots after chemiluminescence detection. In this experiment, C32 cell lysates were loaded on a 10% Bis Tris gel and transferred on both nitrocellulose (NC) and PVDF membranes. Membranes were probed for actin target using rabbit anti-actin primary antibody and GAR-HRP detection antibody. WesternSure ECL, Premium or SuperSignal West Femto substrates were used for recording a chemiluminescence signal on both C-Digit and Odyssey Fc. After imaging, without stripping or reprobing, the blots were washed for less than 30 seconds in PBS and then placed in chemifluorescence substrate in a clamshell (all together) for 5 minutes and then imaged on the Odyssey Clx on auto setting followed by 2 min image acquisition on Odyssey Fc. FIG. 11A shows visual LOD of Actin detection on NC and PVDF using three chemiluminescence substrates. Correspondingly, FIG. 11B displays the visual LOD of Actin by treating the same membranes using chemifluorescence substrate after chemi detection with 30 s rinse with PBS buffer. As observed, the visual LOD is 2~4 times higher than chemiluminescence detection and the fluorescence signal is stable for a long time.

The exemplary detection solution described herein can be used in western blotting applications to detect proteins that are in high abundance and in low abundance. The detection solution is as sensitive or more sensitive than commercially available chemiluminescent substrates. Further, the fluorescence signal can be rescanned for as long a time as needed.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A formulation, the formulation comprising a) a first part and b) a second part:
    a) the first part comprising one or more azines; and
    b) the second part comprising an oxidant, wherein the formulation is free of luminol or luminol derivatives and after admixing the first part and the second part in the presence of a peroxidase the formulation is both fluorogenic and chromogenic.

2. The formulation of claim 1, wherein the one or more azines is 10H-phenothiazine (PTA).

3. The formulation of claim 1, wherein the one or more azines is a mixture of PTA and sodium 3-(phenothiazine-10-yl)propane-1-sulfonate (PTAS).

4. The formulation of claim 1, wherein the oxidant is a member selected from the group consisting of $H_2O_2$, urea-$H_2O_2$ and $NaBO_3$.

5. The formulation of claim 1, wherein the first part further comprises a nucleophilic reagent.

6. The formulation of claim 5, wherein the nucleophilic reagent comprises at least one five- or six-membered ring aryl or heteroaryl, wherein the at least one five- or six-membered ring aryl or heteroaryl can be a fused aryl or heteroaryl.

7. The formulation of claim 6, wherein the nucleophilic reagent comprises an imidazoyl, a pyrazolyl, a triazolyl, a pyridyl, a phenyl, or a phenoyl moiety, which moiety is optionally fused to other rings.

8. The formulation of claim 6, wherein the nucleophilic reagent is a member selected from the group consisting of 4-(1,2,4-triazol-1-yl)phenol, 2-(1H-imidazol-2-yl)pyridine (2-IP), dimethylamino pyridine (DMAP) and 4-morpholinopyridine (MORP).

9. The formulation of claim 8, wherein the nucleophilic reagent is MORP.

10. The formulation of claim 1, wherein the formulation further comprises 2,2'-(hydrazine-1,2-diylidene)bis(3-ethyl-2,3-dihydrobenzo[d]thiazole-6-sulfonate) (ABTS) and or 3-indole acetic acid (IAA).

11. The formulation of claim 1, wherein the first part further comprises a buffer and a solubilizing agent.

12. The formulation of claim 11, wherein the buffer of the first part has a pH of about 3.5 to about 12.

13. The formulation of claim 12, wherein the buffer of the first part has a pH of about 4 to about 11.

14. The formulation of claim 1, wherein the second part further comprises a buffer.

15. The formulation of claim 14, wherein the buffer of the second part has a pH of about 3 to about 9.5.

16. The formulation of claim 15, wherein the buffer of the second part has a pH of about 4 to about 6.

17. The formulation of claim 1, wherein the first part and the second part are in separate containers.

18. The formulation of claim 17, wherein the peroxidase is a moiety having peroxidase-like activity.

19. A method for producing a fluorogenic and chromogenic reaction, said method comprising admixing
    a) a first part of a formulation comprising one or more azines; and
    b) a second part of a formulation comprising an oxidant, wherein the formulation is free of luminol or luminol derivatives and after admixing the first part and the second part in the presence of a peroxidase the reaction is both fluorogenic and chromogenic.

20. A kit for preparing a fluorogenic and chromogenic reaction, the kit comprising:
    a) a first part comprising one or more azines;
    b) the second part comprising an oxidant, wherein upon mixing the first part and the second part the admixture in the presence of a peroxidase, which is free of luminol or luminol derivatives, produces a fluorogenic and chromogenic reaction; and instructions for use.

* * * * *